United States Patent [19]
Simmons et al.

[11] Patent Number: 5,820,374
[45] Date of Patent: Oct. 13, 1998

[54] DENTAL IMPLANT HAVING IMPROVED OSSEOINTEGRATION LATERAL SURFACE

[75] Inventors: William E. Simmons, Miami; Bruce L. Hollander, Boca Raton, both of Fla.

[73] Assignee: Bio-Lok International, Inc., Deerfield Beach, Fla.

[21] Appl. No.: 712,664

[22] Filed: Sep. 16, 1996

[51] Int. Cl.⁶ ..................................................... A61C 8/00
[52] U.S. Cl. ............................................................. 433/173
[58] Field of Search ..................... 433/172, 173, 433/174, 175

[56] References Cited

U.S. PATENT DOCUMENTS 3,717,932  2/1973  Brainin ..................................... 433/175
5,094,618  3/1992  Sullivan ................................... 433/173
5,316,476  5/1994  Krauser .................................... 433/173
5,427,526  6/1995  Fernandes ............................... 433/173

*Primary Examiner*—John J. Wilson
*Attorney, Agent, or Firm*—M. K. Silverman

[57] ABSTRACT

An integral dental implant includes an upper end having an upper surface including an abutment attachment recess extending axially inwardly from the upper surface. The implant also includes an apical end including a lower surface opposite to the upper surface. The implant further includes a substantially cylindrical surface extending between the upper and lower surfaces, the cylindrical surface including a large number of linear grooves which define a substantially diamond-like pattern upon the cylindrical surface. The diamond-like pattern is defined by a combination of substantially circumferential grooves, substantially longitudinal groove, and substantially diagonal grooves.

5 Claims, 2 Drawing Sheets

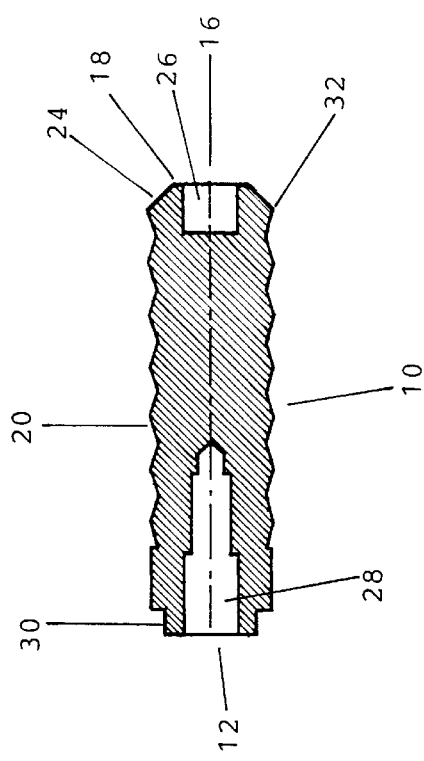
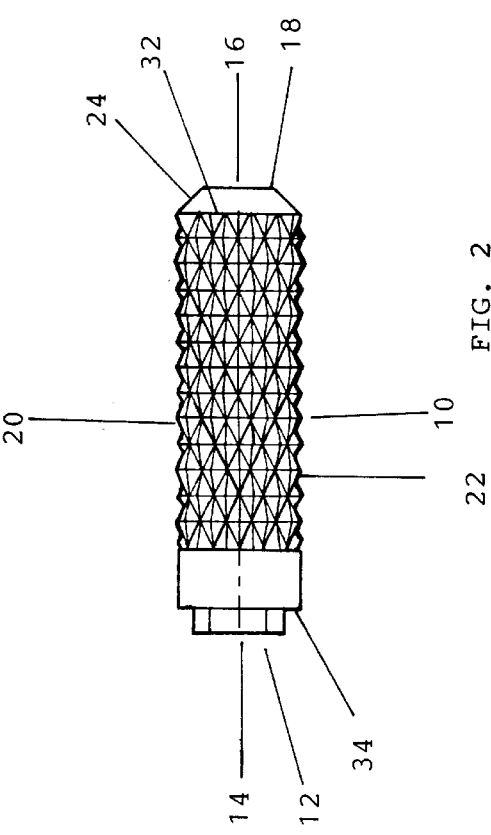
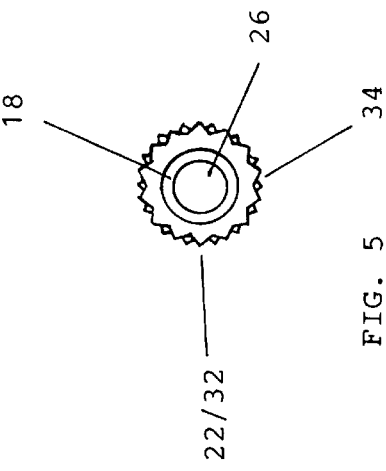
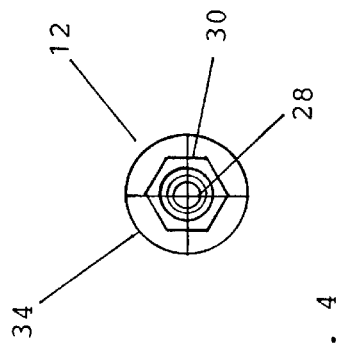

DENTAL IMPLANT HAVING IMPROVED OSSEOINTEGRATION LATERAL SURFACE

BACKGROUND OF THE INVENTION

This invention relates to dental implants using the form of root analogs for the attachment of dental prostheses thereto and, particularly, to such a dental implant having a special-purpose knurled surface, particularly configured for use in areas of normal and relatively low bone density.

Dental implants general implants have been known in the art since at least 1976 with several different designs having been employed. A dental implant is used where there exists missing teeth to act as a root analog that would otherwise support the dental prosthetic device fitting on top of the root, this known as a dental abutment.

Such an implant typically exhibits an internal threaded hole, extending inwardly from a polygonal (typically hexagonal) shaped-top surface, used for the attachment of the dental abutment which is then screwed onto the implant, with a portion thereof engaging the polygonal portion of the implant to prevent rotation thereof. The implant will typically include a generally cylindrical central portion extending from the top portion to a so-called apical portion at the opposite end thereof.

Certain dental implants are provided with helical threaded external cylindrical surfaces and are normally inserted into dense bone areas such as the front jaw. Such implants are screwed into properly sized holes drilled into the bone.

Other dental implants, that are also cylindrically shaped, do not have threads, and are placed into holes previously drilled into the bone. Such non-threaded implants have surface features adapted for attachment to new bone growth. Conventional non-threaded cylindrical implants have openings or flutes extending through their apical portions to form spaces to permit new bone growth. However, research has shown that new bone growth does not predictably fill these openings.

An important function of any implant is to facilitate transmission of forces, generated by chewing and other actions, upon the abutment or prosthesis into forces applied to the bone surrounding the implant, at stress levels compatible with the growth and maintenance of healthy bone tissue. It has been found that such stresses, if properly managed, stimulate surrounding bone which, in the absence of such management would result in eventual atrophy of the bone. However, if the bone is over stimulated, as by improper transmission of forces from the implant, the matrix of the bone or tooth will dissolve, thereby lowering bone density.

There exist in the art numerous dental implants having different geometries upon the cylindrical lateral surfaces thereof. Examples thereof are U.S. Pat. No. 5,316,476 (1994) to Krauser, and U.S. Pat. No. 5,415,545 (1995) to Shaw. However, the prior art, as best known to the inventors, teach the use of implants having either helical grooves or longitudinal channels, in the nature of flutes, to promote osseointegration between the bone and the implant. Each of these approaches have certain limitations thereto. For example, the prior art requires complicated site preparation for insertion of the implant, sufficient surface area to effect optimal osseointegration, and does not provide multi-axis support between the implant and the bone. That is, the prior art of dental implants does not teach a device offering a viable combination of axial, radial and lateral osseointegration and an effective abutment-implant interface along each of said axial, radial and lateral axes.

It is, accordingly, in response to the above set forth long-felt needs in the art that the present invention is directed.

SUMMARY OF THE INVENTION

The invention relates to an integral dental implant comprising an upper end having an upper surface; an apical end including a lower surface, opposite to said upper surface, and a substantially cylindrical surface extending between said upper surface toward said lower surface, said cylindrical portion including a surface having a plurality of linear grooves defining a substantially diamond-like pattern upon said surface. Said upper surface further includes attachment means extending axially inwardly from said upper surface into the body of said implant. Said apical end tapers radially inwardly from the surface of said cylindrical portion to a radius smaller than that of said cylindrical portion.

It is an object of the present invention to provide a dental implant having improved osseointegration between the implant and surrounding bone.

It is another object to provide a dental implant having more active surface bio-integration with bone tissue.

It is a further object to provide an implant of the above type having multi-axial support relative to the bone-implant and abutment-implant interfaces.

It is a still further object of the invention to provide an implant having an expanded surface area to provide greater bio-interfacing surfaces for purposes of osseointegration.

It is a yet further object to provide a dental implant that may be employed with a less complicated site preparation that is required in prior art implants.

The above and yet other objects and advantages of the present invention will become apparent from the hereinafter set forth Brief Description of the Drawings, Detailed Description of the Invention and Claim appended herewith.

DETAILED DESCRIPTION OF THE DRAWINGS

FIG. 2 is a side plan view thereof.

FIG. 3 is an axial cross-sectional view of the implant.

FIG. 4 is a top plan view of the invention.

FIG. 5 is a bottom or apical end plan view thereof.

DETAILED DESCRIPTION OF THE INVENTION

Figure 1:
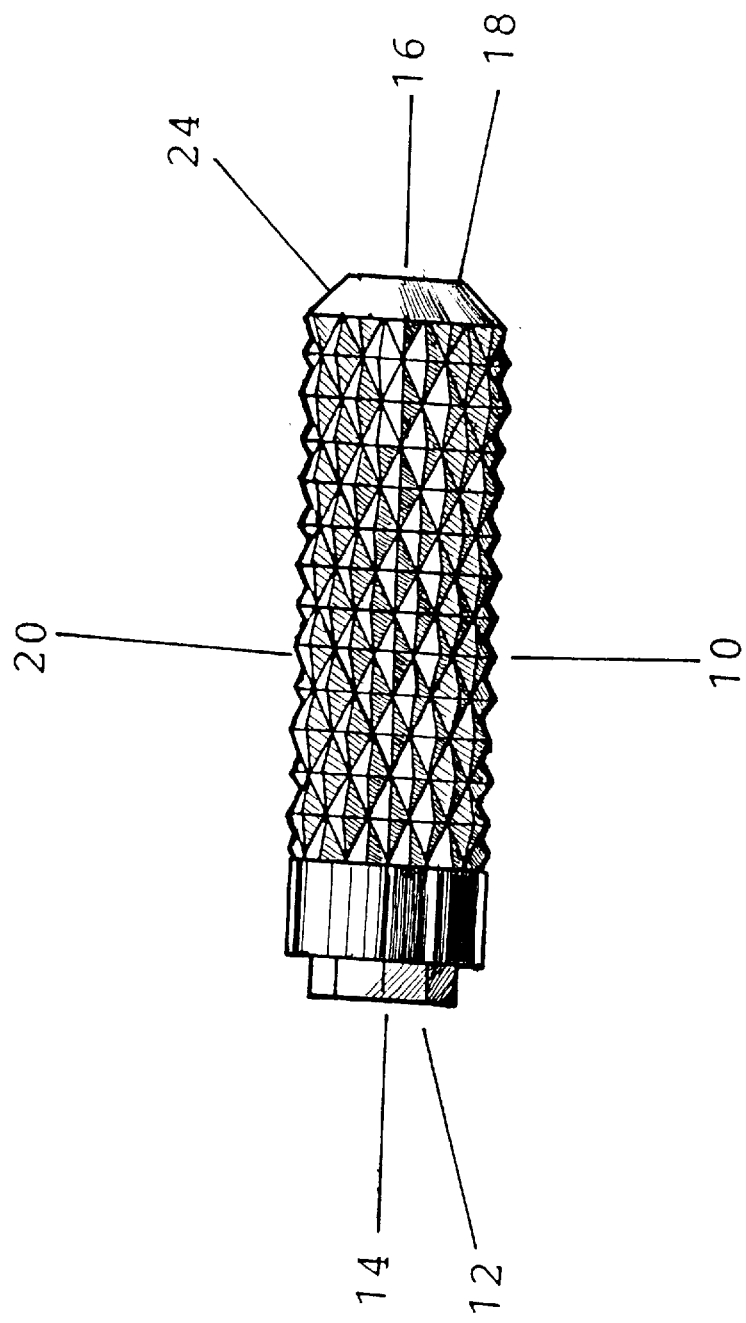
FIG. 1 is a side elevational view of a dental implant made in accordance with the present invention.

With reference to the figures, the instant inventive implant 10 may be seen to include an upper end 12 having an upper surface 14, a apical end 16 including a lower surface 18.

The instant implant also includes a generally cylindrical central portion 20 having a lateral surface 22 which is characterized by a matrix of orthonormal and diagonal grooves which interact to produce a generally diamond shaped pattern as may be more particularly noted in the perspective view of FIG. 1 and the plan view of FIG. 2.

It is further noted that the cylindrical portion 20, as it approaches the apical end 16 of the implant, includes a truncoconical portion 24 in which the radius of the implant gradually reduces to the radius of the lower surface 18 of the apical end.

As may be further noted in the views of FIGS. 3 and 5, the lower surface 18 of the apical end 16 includes an apical vent 26, the purpose of which is to accommodate any excess bone or other tissue which has not been fully removed from the preparation site, this causing "back pressure relief" resulting in ease and accuracy of installation.

At the upper end 12 of the implant there is provided an axial cavity 28 (see FIG. 3) into which the abutment, i.e., the dental prosthesis, to be secured to the implant is to be inserted. Further shown at the upper end 12 of the implant is attachment means 30, this typically in the form of a hex or polygonal surface to facilitate locking of the abutment into the implant.

With further reference to FIGS. 2 and 5, it is noted that there exists an interface 32 between the beginning of the truncoconical portion 24 and the cylindrical surface 22. At this interface 32, the intersection of said truncoconical portion and the diamond-like cylindrical surface 22 results in a multiplicity of irregular flute-like grooves 34 which (a) facilitate the implant insertion process by relieving back pressure at the preparation site, (b) improve seating of the implant at the site, and (c) assist and the later osseointegration of the implant at the implant site. Prior art designs of implants do not allow for venting or relief of pressure build-up at the insertion site.

It should be appreciated that the implant base material may be formed of various grades of titanium, these including without limitation ASTMB 348 Grade 5-6 AL 4V. The implant may be formed in various diameters and length. The surface thereof will typically be treated with RBM, H/A, or TPS.

The diamond shaped surface 22, also known as a knurled surface, may be formed in a variety of ways including, without limitation, rolling and machining of the grooves and the imparting of angular cross cuts onto cylindrical surface 20 of the implant.

It is to be understood that the diamond knurled-shaped surface 22 provides enhanced support and osseointegration at the implant bone interface, which enhanced support furnishes a superior foundation upon which to mount the abutment or prosthesis of interest. More particularly, it has been found that the pattern of longitudinal circumferential and lateral diagonal lines, which characterize surface 22, each provide a different form of support which, taken in combination, yield a synergy of function not known in the art. More particularly, it is to be appreciated that the circumferential lines on surface 22 protect against movement in the axial direction, the longitudinal lines of the pattern provides resistance to polar movement of the implant while the diagonal lines provide general resistance to any torque or bending moment to which any th axis of the implant is subjected. Accordingly, there is provided a system of multi-axial support for the abutment which is secured to the subject implant. In addition, the particular diamond knurled pattern shown in FIGS. 1 and 2 has been found to provide a more active surface bio-integration with the bone. As may be appreciated from the geometry of the knurled surface, which comprises a multiplicity of diamond-like wedges, provides a greatly expanded surface area over which osseointegration can occur.

It is to be further understood that an implant produced in accordance with the present invention may include, at surface 34 (see FIGS. 2 and 4) concave seating faces as is taught by U.S. Pat. No. 5,447,434 and, with respect to the interlock between an abutment and the instant implant within cavity 28, may use the journal lock structure taught in U.S. Pat. No. 5,415,545.

It has been found that, because of the excellent osseointegration and expanded bio-interfacing surfaces afforded by the present implant, bone site preparation is less complicated. Also, the particular diamond shaped surface of the present implant increases the efficiency of the state-of-the-art bio-retention coatings.

It is also to be appreciated that the diamond-like surface shown in FIGS. 1 and 2 may, within the scope of the present invention, define other geometries including, without limitation, squares, triangles and parallelograms.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

Having thus described our invention what we claim as new, useful and non-obvious and, accordingly, secure by Letters Patent of the United States is:

1. An integral dental implant, comprising:
   (a) an upper end having an upper surface including abutment attachment means extending axially inwardly from said upper surface;
   (a) an apical end including a lower surface opposite said upper surface; and
   (c) a substantially cylindrical surface extending between said upper and lower surfaces, said cylindrical surfaces including a multiplicity of linear grooves defining a substantially diamond-like pattern upon said cylindrical surface.

2. The dental implant as recited in claim 1, in which said upper surface includes a rotational wrench-engagement surface.

3. The dental implant as recited in claim 1, in which a principal diameter of said lower surface of said apical end comprises a smaller diameter than that of said cylindrical surface, and in which said lower surface communicates with said cylindrical surface through an integral truncoconical segment.

4. The dental implant as recited in claim 3, in which said apical end includes an axial recess.

5. The dental implant as recited in claim 3, in which an interface between said truncoconical segment and said cylindrical portion defines a multiplicity of polar flutes at lower ends of said longitudinal and diagonal grooves of said cylindrical surface.

* * * * *